US00PP22478P2

(12) United States Plant Patent
Korlipara

(10) Patent No.: US PP22,478 P2
(45) Date of Patent: Jan. 31, 2012

(54) ***COREOPSIS* PLANT NAMED 'CITRINE'**

(50) Latin Name: ***Coreopsis* spp.**
Varietal Denomination: Citrine

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/927,262

(22) Filed: Nov. 9, 2010

(51) Int. Cl.
*A01H 5/00* (2006.01)

(52) U.S. Cl. ..... Plt./417

(58) Field of Classification Search ..... Plt./417
See application file for complete search history.

*Primary Examiner* — Annette Para
(74) *Attorney, Agent, or Firm* — Klarquist Sparkman, LLP

(57) ABSTRACT

A new and distinct *Coreopsis* plant named 'Citrine' characterized by daisy-type flowers that grow to 4 cm in diameter, flowers that are clear yellow, grass green foliage on short stems, flowers all summer, a dense, compact, mounding habit, and excellent vigor.

1 Drawing Sheet

Botanical denomination: *Coreopsis* spp.
Variety designation: 'Citrine'.
Parentage: *Coreopsis* 'Rum Punch' (U.S. Plant Pat. No. 18,889)×*C. pubescens.*

BACKGROUND OF THE INVENTION

The present invention relates to a new and distinct *Coreopsis* and given the cultivar name 'Citrine'. *Coreopsis* is in the family Asteraceae. This new cultivar originated from a controlled cross of *Coreopsis* 'Rum Punch' (U.S. Plant Pat. No. 18,889) as the seed parent and *Coreopsis pubescens*, an unpatented plant, as the pollen parent. The breeding program is to produce hardy dwarf cultivars.

Compared to the seed parent, *Coreopsis* 'Rum Punch', the new cultivar has flowers that yellow rather than orangey-rose and the habit is smaller and tighter. Compared to the pollen parent, *Coreopsis pubescens*, the new cultivar has flowers that are a lighter yellow and leaves that are much narrower. The habit is smaller and tighter.

Compared to *Coreopsis grandiflora* 'Presto', an unpatented plant, the new variety has single flowers of clear yellow rather than a golden doubles.

SUMMARY OF THE INVENTION

The following traits have been repeatedly observed and are determined to be the unique characteristics of the new variety. These characteristics in combination distinguish *Coreopsis* 'Citrine' as a new and distinct cultivar:

1. daisy-type flowers that grow to 4 cm in diameter,
2. flowers that are clear yellow,
3. grass green foliage on short stems,
4. flowering for the whole summer,
5. a dense, compact, mounding habit, and
6. excellent vigor.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPH

The photograph shows one-year-old *Coreopsis* 'Citrine' growing in the ground in the trial field in August in Canby, Oreg.

DETAILED PLANT DESCRIPTION

The following is a detailed description of the new *Coreopsis* cultivar based on observations of four-month-old specimens growing in a four inch pots in a warm greenhouse in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart, $5^{th}$ edition.

Plant:
- *Type.*—Herbaceous perennial.
- *Hardiness.*—USDA Zones 7 to 9.
- *Size.*—22 cm wide and 23 cm tall to top of inflorescences.
- *Form.*—Mound.
- *Vigor.*—Excellent.
- *Roots.*—Fibrous, stems root easily from stem cuttings.

Stem:
- *Type.*—Ascending.
- *Size.*—13 cm tall to where branches for flowering and 4 mm wide.
- *Number of stems from the crown.*—2 to 4.
- *Internode length.*—1 to 3 cm.
- *Surface.*—Pubescent.
- *Color.*—Green 137A.

Leaf:
- *Type.*—Simple.
- *Shape.*—Ovate, 1 to 5 pinnate, pinnae linear lanceolate.

*Arrangement.*—Opposite.

*Size.*—Grows to 14 cm long and 5.5 mm wide.

*Apex.*—Acute.

*Margins.*—Entire.

*Petiole.*—Grows to 5.5 cm long 1 to 2 mm wide, pubescent, Green 137A.

*Surface texture.*—Pubescent on top and bottom sides.

*Venation.*—Pinnate.

*Color.*—Topside Green N137A, bottom side Green N137B.

Inflorescence:

*Type.*—Long stalked terminal heads of daisy type inflorescences.

*Peduncle.*—Grows to 6 cm long, 1 mm wide, glabrous, Green 137A.

*Size.*—Grows to 4.2 cm wide and 9 mm deep.

*Immature.*—Globular, 7 mm wide and 6 mm deep, Yellow Green 152A on the sides and Yellow Green 153C on top, glabrous.

*Receptacle.*—Disc shaped, 3 mm wide and 1.5 mm deep, Green 148B.

*Phyllaries.*—In 2 series; first series closet to ray florets 5 mm deep and 15 mm wide, 8 in number, each 5.5 mm long and 3.5 mm wide, ovate, margin entire, tip acute, glabrous on both sides, both sides Yellow Green 152A; lower series in an area 3 mm deep and 8 mm wide, 5 in number, 3 mm long and 1.5 mm wide, each ovate, margin entire, tip acute, both sides glabrous and Yellow Green 146A.

*Lastingness.*—Each inflorescence lasts about a week on the plant.

Florets:

*Type.*—Composite.

*Ray florets.*—8 in number with no pistil or stamen, grows to 18 mm long, 7 mm wide, obovate, with the tip three-lobed with lobe tips obtuse and the central lobe the longest, sometimes notched, margins entire, glabrous on both sides; topside Yellow 9A, bottom side Yellow 9B.

*Disc.*—Conic, deeper with maturity, 8 mm wide and becoming 3 mm deep with maturity, after opening Yellow Orange 21A.

*Disc florets.*—Tubular, with stamen and pistil, about 110 in number, 5 mm long and 1 mm wide, tubular; corolla 2.5 mm long, Yellow 13B; pistil 1, 5 mm long, ovary 1 mm long, Green Yellow 1C, style 5 mm long, with extruding, 2-branched stigma, stigma and style Yellow 13B; stamen 5, anthers 1.2 mm long, Greyed Brown N199 B, no pollen, male sterile.

*Bloom period.*—June through September in Canby, Oreg.

*Fragrance.*—Light, Chrysanthemum-like.

*Seed.*—None seen.

*Fertility.*—Sterile.

Disease and pests: *Coreopsis* are susceptible to mildew and fungal spots. No resistance is known for this variety.

I claim:

1. A new and distinct *Coreopsis* plant as herein illustrated and described.

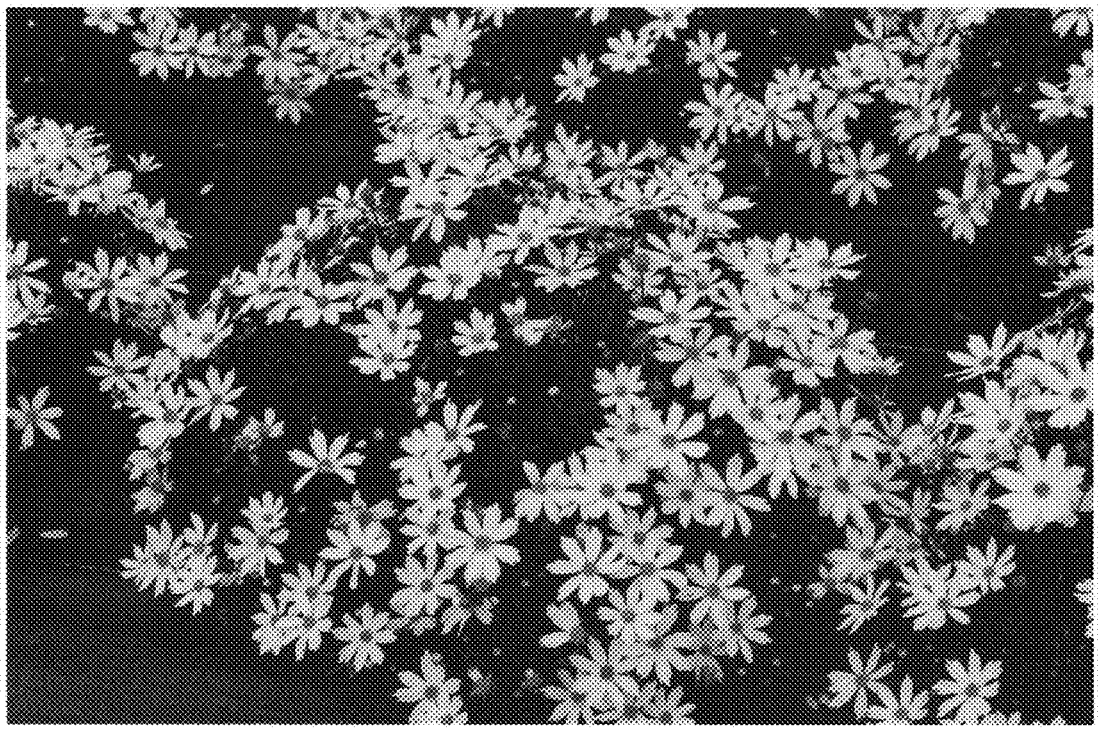

* * * * *